(12) United States Patent
Negrelli

(10) Patent No.: US 6,200,024 B1
(45) Date of Patent: Mar. 13, 2001

(54) VIRTUAL C-ARM ROBOTIC POSITIONING SYSTEM FOR USE IN RADIOGRAPHIC IMAGING EQUIPMENT

(75) Inventor: Donald E. Negrelli, Gates Mills, OH (US)

(73) Assignee: Picker International, Inc., Highland Heights, OH (US)

( * ) Notice: Subject to any disclaimer, the term of this patent is extended or adjusted under 35 U.S.C. 154(b) by 0 days.

(21) Appl. No.: 09/200,688

(22) Filed: Nov. 27, 1998

(51) Int. Cl.[7] .................................................. H05G 1/02
(52) U.S. Cl. ............................ 378/197; 378/196; 378/198
(58) Field of Search ............................... 378/197, 198, 378/62, 196, 4

(56) References Cited

U.S. PATENT DOCUMENTS

| | | | |
|---|---|---|---|
| 4,139,776 | 2/1979 | Hellstrom | 378/197 |
| 4,358,856 | * 11/1982 | Stivender et al. | 378/197 |
| 4,365,343 | * 12/1982 | Grady et al. | 378/181 |
| 4,756,016 | * 7/1988 | Grady et al. | 378/197 |
| 4,807,273 | 2/1989 | Haendle | 378/197 |
| 4,894,855 | 1/1990 | Kresse | 370/196 |
| 5,078,140 | * 1/1992 | Kwoh | 378/20 |

FOREIGN PATENT DOCUMENTS

| | | |
|---|---|---|
| 90 02 129 U | 6/1990 | (DE) . |
| 90 12 435 U | 1/1992 | (DE) . |
| 0 220 501 | 5/1987 | (EP) . |
| 2 645 007 | 10/1990 | (FR) . |

OTHER PUBLICATIONS

European Search Report dated Oct. 3, 2000.

* cited by examiner

*Primary Examiner*—David V. Bruce
*Assistant Examiner*—Drew A. Dunn
(74) *Attorney, Agent, or Firm*—Fay, Sharpe, Fagan, Minnich & McKee, LLP

(57) ABSTRACT

A virtual C-arm support system 40 is used in a radiographic imaging apparatus of the type including an x-ray source 44 and an x-ray detector 48. The support system includes a first positioning system 42 operatively connected to the x-ray source for selectively positioning the x-ray source in a range of first orientations 120, 140, 170 relative to the examination region E. A second positioning system 46 is operatively connected to the x-ray detector 48 for selectively positioning the x-ray detector in a range of second orientations 122, 142, 172 relative to the examination region E. A control unit 60 is in operative command of at least one of the first and second positioning systems to maintain a predetermined spatial relationship between the x-ray source and the detector for each of the ranges of the first and second orientations relative to the examination region. In a second embodiment, the control unit is in operative command of only the first positioning system, the second positioning system being manually movable. The control unit maintains a predetermined spatial relationship between the x-ray source and detector by moving the x-ray source in response to manual movement of the x-ray detector for each of the ranges of first and second orientations of the source and detector relative to the examination region.

24 Claims, 7 Drawing Sheets

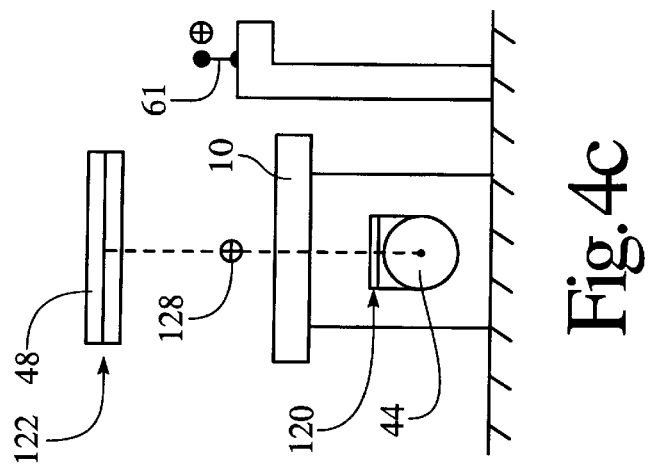
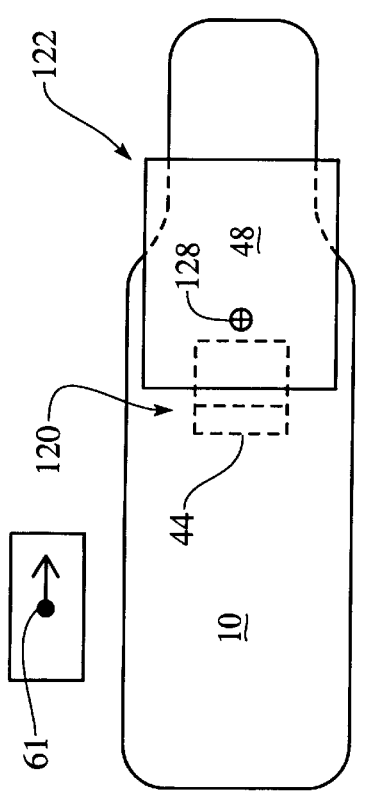
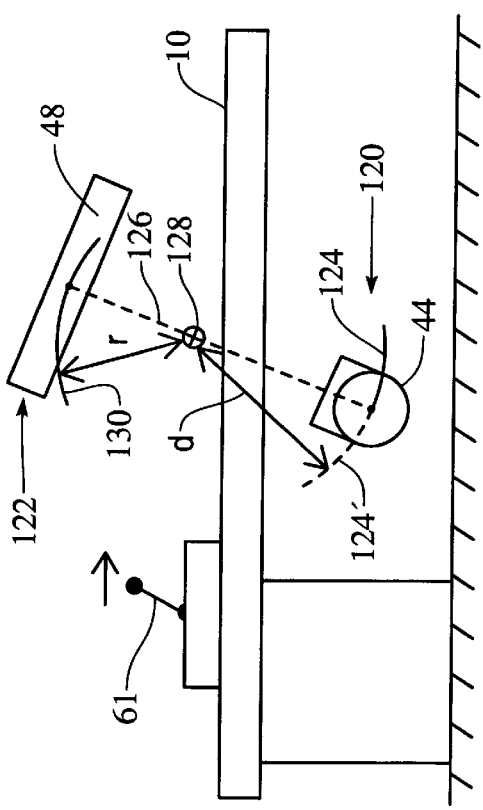

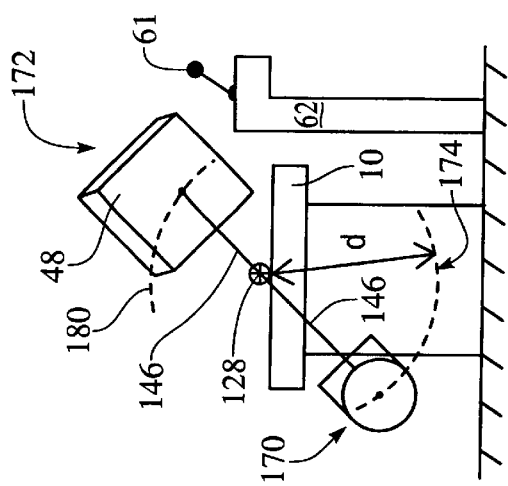
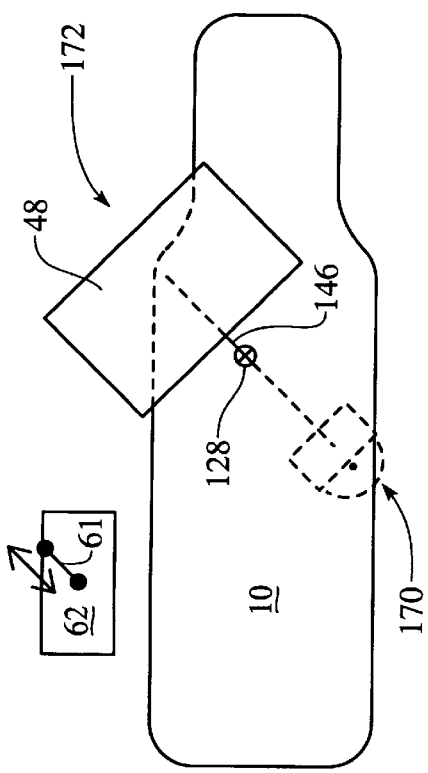
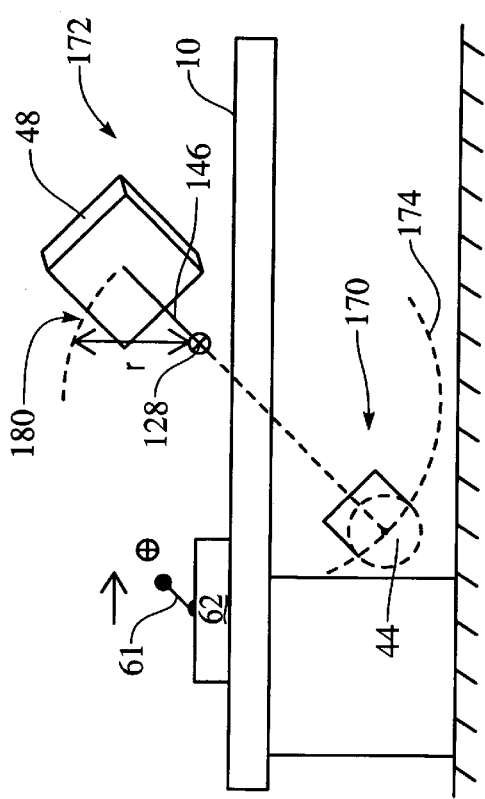
Fig.6a
Fig.6b
Fig.6c

VIRTUAL C-ARM ROBOTIC POSITIONING SYSTEM FOR USE IN RADIOGRAPHIC IMAGING EQUIPMENT

BACKGROUND OF THE INVENTION

The present invention is directed to the art of radiographic medical imaging and, more particularly, to a robotic support system for positioning an x-ray source and receptor pair relative to an examination region to generate and transmit an x-ray beam through the examination region. The invention finds particular application in conjunction with imaging or interventional procedures that have heretofore been performed in association with C-arm or L/U-arm fluoroscopic x-ray systems and will be described with particular reference thereto. It is to be appreciated, however, that the invention is also applicable to a wide range of other medical or industrial imaging apparatus that operate through the use of spaced apart radiographic energy source and receptor pairs to monitor or image a region of a patient or other item disposed between the source and receptor pair.

In some operating rooms, such as operating rooms for vascular catheter procedures, a projection x-ray imaging device is provided in association with an operating table. More specifically, an x-ray tube or generator and an x-ray detector are mounted on a C-arm which is positioned such that a patient or an area of interest lies between the x-ray source and receptor. The x-ray source and receptor are rotatable and longitudinally displaceable as a unit to select a region and angle for projection imaging. Once the surgeon has positioned the x-ray source and detector in the proper position, the surgeon actuates the x-ray tube sending x-rays through the patient and onto the x-ray detector for a preselected exposure time. The x-rays received by the detector are converted into electric video image data signals representing a projection or shadow-graphic image. The projection or shadow-graphic image is stored electronically or displayed on a video monitor which is viewable by the physician.

One such prior art imaging system is shown in FIG. 1. As illustrated, a C-arm C is supported by a curved support carriage A adjacent an examination region E. The examination region E is describable by orthogonal axes X, Y, and Z. An x-ray transparent couch 10 is positioned such that a region of interest of a subject lying upon the couch is positioned in the examination region E.

The rotational support assembly A includes a rotational mount or bearing 14 mounted to a fixture for rotation about a horizontal axis X. The rotational mount 14 can be movably fixed to a track or other mechanism 18 to also allow movement of the mount in the Y and Z directions.

The midpoint 22 of the C-arm C is rotatably attached to the bearing 14. The C-arm C defines two opposing parallel ends 24, 26 on either side of the examination region E. A detector 28, such as a flat panel detector or the like for detecting x-ray radiation, is attached to the first end 24. Common detectors include solid state devices, such as a grid of amorphous silicon detector elements for generating x-ray intensity signals for each element on the grid. An x-ray source 30 is attached on the second end 26 of the C-arm. The C-arm C has sufficient size and bulk to maintain the detector 28 and the x-ray source 30 within a fairly repeatable fixed spatial relationship.

In the system shown, the curved support carriage A is adapted to permit rotational movement of the x-ray source and detector along an arcuate path B to enable left and right anterior oblique image views to be collected. The bearing mount 14 enables cranial and caudal image views to be collected. Compound anterior oblique, cranial, and caudal views can be collected by moving the mechanical C-arm system C carriage support and bearing mount into the appropriate respective orientations.

Due to the mass of the x-ray tube and the weight of the detector carried on opposite ends of the C-arms, the curved support assembly is designed to provide adequate support and rigidity and, therefore, is large and bulky. Similarly, the C-arm assembly C is necessarily large in order to enable head to toe imaging capabilities of a patient disposed between the x-ray source and detector.

During most interventional procedures, the C-arm and curved support carriage A obstruct access to the patient because of their size. The awkwardness of the mechanical support system can cause confusion in the operating room when the surgical procedure requires gross movements of the components such as, for example, when it is necessary to first image the head area, followed by an image of the foot area of the patient. Using the above mechanical system it is also awkward and inconvenient to rotate the C-arm C from the vertical orientation shown in FIG. 1 to either the left or right anterior oblique views.

It is therefore desirable to provide a virtual C-arm support system that has all of the functionality of the prior C-arm system described above, including the carriage and orbit motions, but without the bulky and inconvenient overhead rotational support assembly or the C-arm member rotatably attached to the support assembly.

The present invention provides a new and improved method and apparatus which overcomes the above referenced problems in the prior art and others by eliminating the inconvenient overhead support arm and C-shaped structures found in the prior art systems.

SUMMARY OF THE INVENTION

In accordance with the present invention, a robotic support system is provided for use in a radiographic imaging apparatus of the type including an x-ray source adapted to transmit an x-ray beam along a path through an examination region and an x-ray detector adapted to receive the x-ray beam and generate electric signals indicative of an intensity of the received x-ray beam. The robotic support system includes a first positioning system connected to the x-ray source for selectively positioning the x-ray source in a range of first orientations relative to the examination region. A second positioning system is included and is connected to the x-ray detector for selectively positioning the x-ray detector in a range of second orientations relative to the examination region. The first and second positioning systems are independently operable and are connected to a control unit for coordinating their relative movements and positions. The control unit is in operative command of at least one of the first and second positioning systems to maintain a predetermined spatial relationship between the x-ray source and the x-ray detector for each of the ranges of first and second orientations of the source and receptor relative to the examination region.

In accordance with a more limited aspect of the invention, the robotic support system provides a virtual C-arm support system having all of the capabilities of the prior art mechanical C-arm imaging devices but without the bulky mechanical joints and arms.

In accordance with yet a more limited aspect of the invention, the control unit of the virtual C-arm support system is in operative command of both the first positioning system and the second positioning system and is adapted to selectively generate the first and second command signals to respectively position the x-ray source and the x-ray receptor at a plurality of sets of first and second positions in relative alignment with each other on opposite sides of the examination region. The control unit generates the first and second command signals in a manner that the x-ray source and the x-ray receptor are positioned in relative alignment with each other on opposite sides of the examination region at each of the plurality of sets of first and second positions. Further, the first and second command signals are generated by the control unit to position the x-ray source so that the x-ray beam transmitted from the x-ray source passes through the examination region. Still further, the first and second command signals are generated by the control unit in a manner to control the second positioning system so that the x-ray detector is disposed along the path of the x-ray beam to intercept the x-ray beam and generate electric signals indicative of the intensity of the received x-ray beam.

In accordance with yet a more limited aspect of the invention, the first positioning system is a first movable arm assembly having a first end held fixed relatively to the examination region and a free end adapted for connection to the x-ray source. The second positioning system is a second movable arm assembly having a first end held fixed at a second location relative to the examination region and a free end adapted for connection to the x-ray detector. The first and second movable arm assemblies are responsive to the first and second command signals, respectively, from the control unit to selectively orient the x-ray source and the x-ray detector relative to the examination region.

In accordance with still yet a further aspect of the invention, the second positioning system is adapted to generate an x-ray receptor orientation feedback signal representative of the relative orientation between the x-ray detector carried on the second positioning system and the examination region. The control unit is in operative control of the first positioning system and is adapted to selectively generate the first command signal used by the first positioning system to position the x-ray source to control the path of the x-ray beam transmitted through the examination region based on the x-ray detector feedback orientation signal. The control unit moves the x-ray source carried on the first positioning system to maintain a predetermined spatial relationship between the x-ray source and the x-ray detector.

The primary advantage of the present invention is improved patient accessibility. The x-ray source and detector devices are supported from points below and above the patient, respectively, to enable unobstructive lateral access to the patient.

Another advantage of the invention is that the x-ray source is supported on a multi-axis rotation arm attached to the floor beneath the patient couch and the x-ray detector is supported on a second multi-axis robotic arm attached to the ceiling above the patient couch. This arrangement affords maximum access to the patient and the robotic arms make the overall radiographic imaging systems particularly useful during interventional procedures.

Yet another advantage of the present invention is a radiographic imaging apparatus that is smaller in size than prior imaging apparatus.

Still other advantages and benefits of the invention will become apparent to those skilled in the art upon a reading and understanding of the following detailed description.

BRIEF DESCRIPTION OF THE DRAWINGS

The invention may take physical form in certain parts and arrangements of parts, the preferred embodiments of which will be described in detail in this specification and illustrated in the accompanying drawings which form a part hereof, and wherein:

FIGS. 4a–4c show top, side, and end plan views of the robotic x-ray source and detector positioning system according to the present invention disposed in a first orientation;

FIGS. 6a–6c show top, side, and end plan views of the robotic x-ray source and detector positioning system according to the present invention disposed in a third orientation;

DETAILED DESCRIPTION OF THE PREFERRED EMBODIMENTS

Figure 1:
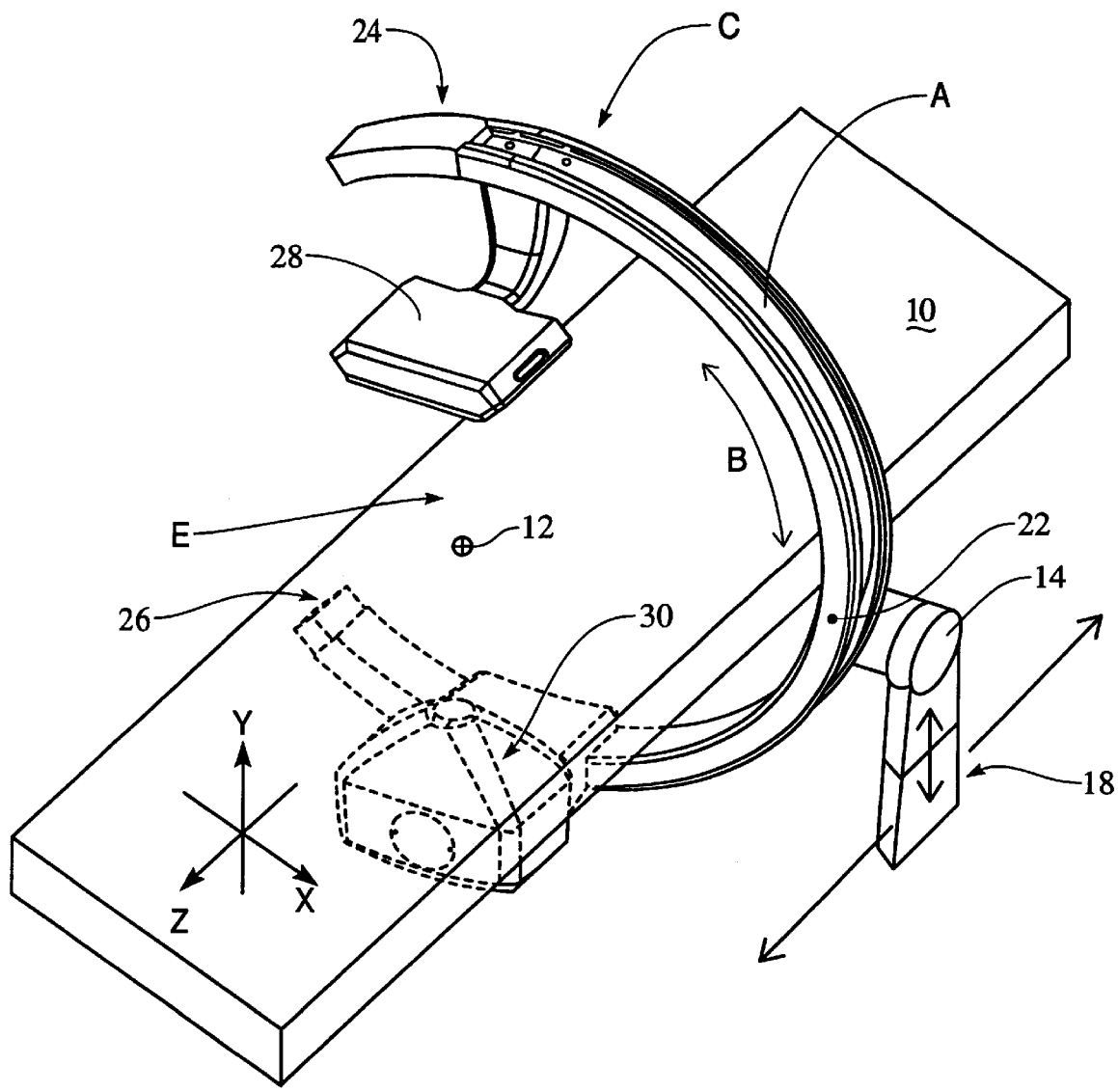
FIG. 1 is diagrammatic illustration of a prior art C-arm radiographic imaging system.
Figure 2:
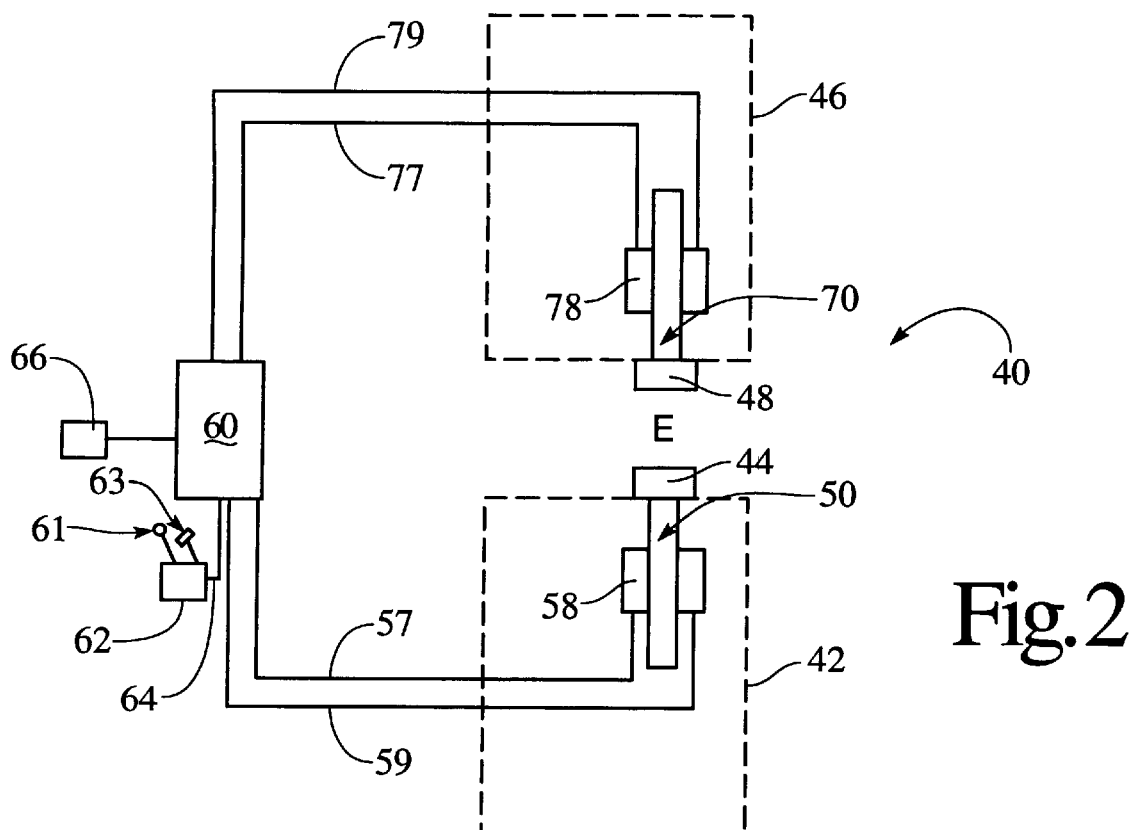
FIG. 2 is a block diagram of a virtual C-arm robotic positioning system formed in accordance with a first preferred embodiment of the present invention.
Figure 3:
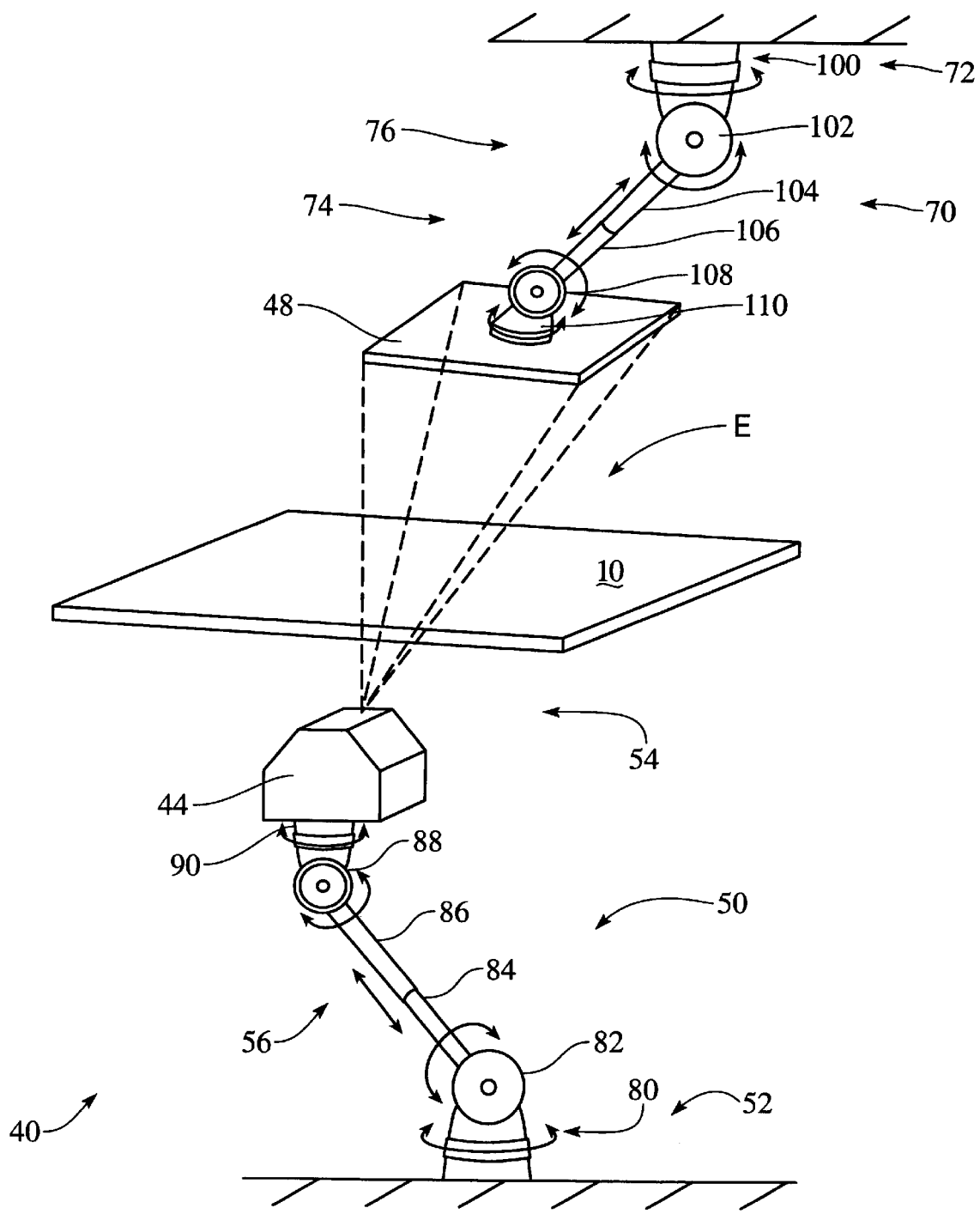
FIG. 3 is a diagrammatic illustration of the first and second embodiments of the invention with the robotic arms shown in a parked or a ready orientation.

Referring now to the drawings wherein the showings are for the purposes of illustrating the preferred embodiments of the invention only and not for purposes of limiting same, FIGS. 2 and 3 shows a virtual C-arm support system 40 formed in accordance with the present invention. The support systems includes a first positioning system 42 operatively connected to an x-ray source 44 and a second positioning system 46 operatively connected to an x-ray detector 48. The first and second positioning systems are each adapted to selectively position the x-ray source and detector, respectively, in a range of positions relative to the examination region. To that end, the first positioning system 42 includes a first movable arm assembly 50 having a first end 52 held fixed at a first location relative to an examination region E. A free end 54 of the first movable arm assembly 50 is adapted for direct mechanical connection to the x-ray source 44. The movable arm assembly includes multiple rotatable, extendable, and pivotable arm segments 56 to be described in greater detail below and a closed loop servo positioning system 58 for controlling the movement and positioning of the movable arm assembly 50 in response to command signals 57 generated by a control unit 60.

Similarly, in accordance with the first preferred embodiment of the invention, the second positioning system 46 includes a second movable arm assembly 70 having a first end 72 held fixed at a second location relative to the examination region E and a free end 74 adapted for direct mechanical connection to the x-ray detector 48. The second movable arm assembly 72 includes multiple rotatable, extendable, and pivotable arm segments 76 to be described in greater detail below and a second closed loop servo positioning system 78 that is responsive to second command signals 77 generated by the control unit 60 to move the second movable arm assembly and position the x-ray receptor relative to the examination region E and the relative to the x-ray source.

In accordance with the first preferred embodiment of the invention, the first and second positioning systems 42, 46 operate independent of each other but under the command of the control unit 60. The control unit is in operative command of both positioning systems to maintain a predetermined spatial relationship between the x-ray source and detector for a range of positions of those devices relative to the examination region. The range of positions include all of the positions that were heretofore enabled by the prior carriage support C-arm systems described above.

A joystick device 62 is connected to the control unit 60. A pair of joystick handles 61, 63 enable a human operator to effect motion and positioning commands. The joystick generates x-ray beam angulation signals 64 that are used by the control unit 60 to orient the x-ray source and detector carried on the movable arm assemblies into various suitable positions relative to the examination region to obtain radiographic images of a patient. A position display device 66 is connected to the control unit to generate human readable indicia reporting the position and orientation of the x-ray source and detection device carried on the first and second positioning systems.

With particular reference now to FIG. 3, the first and second movable arm assemblies 50, 70 are shown in their respective parked or ready orientations relative to the patient couch 10 and examination region E. Further, the figure illustrates the multiple rotatable, extendable, and pivotable arm segments of each of the first and second movable arm assemblies in greater detail. In that regard, the first movable arm assembly 50 includes a rotatable base portion 80 that supports a pivot joint 82 as shown. A pair of telescopically extendable arm members 84, 86 are carried on the pivot joint 82. The upper extendable arm member 86 is connected to a second pivot joint 88 that is in turn rotatably attached to an x-ray source support connector 90. As illustrated, the support connector 90 is adapted for direct mechanical connection to the x-ray source 44. The multiple arm segments 56 of the first robotic arm assembly 50 are movable in directions shown by arrows in the figure.

Preferably, movement of each of the rotatable members 80, 90 as well as the joint members 82, 88, and the extendable arm members 84, 86 is motivated by one or more electric positioning motors (not shown) that are connected to their respective movable members or joints using suitable gears, pulleys, (not shown) and the like. In addition, each of the rotatable, pivotable, and extendable members are operatively associated with one or more feedback devices that generate a set of respective feedback position signals 59 (FIG. 2) used by the control unit to generate position command signals 57.

In the first preferred embodiment, the position command signals are generated by the control unit based on a difference between the desired position derived from the joystick device 62 and an actual position derived from the feedback signals. The position command signals are used by the electric positioning motors (not shown) to operatively drive the multiple arm segments 56 of the first movable arm assembly 50 so that the x-ray source and detector are suitably positioned and properly oriented relative to the examination region.

With continued reference to FIG. 3, the second movable arm assembly 70 is preferably formed as a mirror image of the first movable arm assembly 50. In that regard, the second movable arm assembly includes a first fixed end 72 attached to the ceiling above the x-ray transparent couch 10 as shown. A rotatable base portion 100 carries a first pivot joint 102 which is in turn connected to a pair of extendable arm members 104, 106. The outer extendable arm member 106 is attached to a second pivot joint 108 which is in turn rotatably connected to an x-ray detector support connector 110. The x-ray detector support connector is adapted for direct mechanical attachment to the x-ray detector 48 as shown.

As with the first movable arm assembly 50 discussed above, the second movable arm assembly 70 includes a set of electric positioning motors (not shown), preferably one at each movable interface, to enable the positioning of the x-ray detector in a range of second orientations relative to the examination region. In addition, each of the rotatable, pivotable, and extendable members of the second movable arm assembly 70 are operatively associated with one or more feedback devices (not shown) that generate feedback position signals 79 (FIG. 2) used by the control unit to generate position command signals 77. The position command signals are generated by the control unit based on a difference between the desired position derived from the x-ray beam angulation signal 64 and an actual position of the x-ray source and detector derived from the feedback signals 57 and 77. The position command signals are used by the electric positioning motors (not shown) to operatively drive the multiple arm segments 76 of the second movable arm assembly 70 so that the x-ray detector is suitably positioned and properly oriented relative to the examination region and relative to the x-ray source 44.

FIGS. 4a–4c show top, side, and end schematic plan views of the robotic virtual C-arm support system 40 in a first operative position in accordance with the first preferred embodiment of the present invention. As can be seen, the x-ray source and detector pair have been moved from the ready position illustrated in FIG. 3 to a set of first and second positions 120, 122 relative to the examination region through actuation of the first joystick 61 in the direction shown.

As noted above, an x-ray beam angulation signal is generated by the joystick device 62 (FIG. 2) for use by the control unit 60 to in turn generate the first and second command signals 57, 77, respectively. The command signals are interpreted by the first and second servo systems 58, 78 to move the x-ray source and detector pair carried on the first and second positioning systems in place as shown in FIGS. 4a–c. In addition to the above, the control unit 60 is adapted to generate the first and second command signals so that the x-ray source and detectors are moved into place simultaneously in a coordinated fashion. More particularly, in FIGS. 4a–4c, the x-ray source 44 is moved toward the foot end of the couch 10 along an arcuate path 124 so that the central ray of the x-ray beam defines an x-ray path 126 that passes through the isocenter 128 while maintaining a constant distance d from the isocenter. The x-ray detector is moved into the second position 122 shown based on the second command signals 77 from the control unit 60 along an arcuate path 130 so that the receptor maintains a constant distance r from the isocenter 128 while maintaining a perpendicular relationship between the flat face of the detector and the central ray of the x-ray beam defining the x-ray path 126.

In accordance with FIG. 4a–c, therefore, movement of the first joystick 61 along the direction shown urges the first and second movable arm assemblies to move the x-ray source and detector pair into a plurality of sets of first and second positions relative to the examination region and patient support couch to enable cranial and caudal radiographic images to be generated. Preferably, the control unit is responsive to motion of the first joystick in a manner that the x-ray source and detector are moved until the first joystick is returned to its neutral or center position or, alternatively, until the source or detector reach the end of mechanical travel.

Figure 5C:
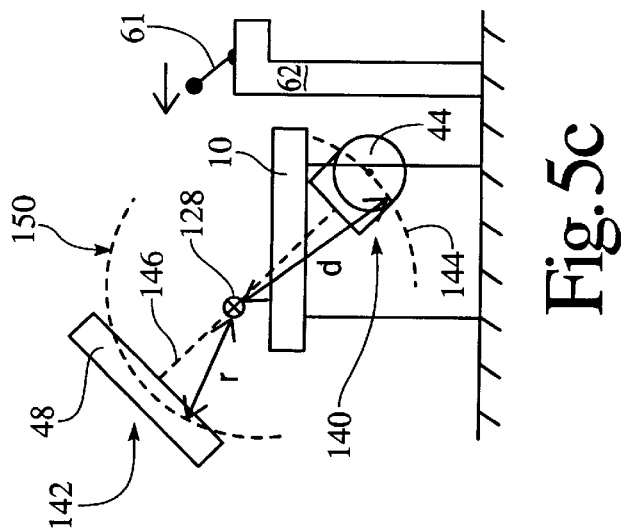
FIGS. 5a–5c show top, side, and end plan views of the robotic x-ray source and detector positioning system according to the present invention disposed in a second orientation.
Figure 5A:
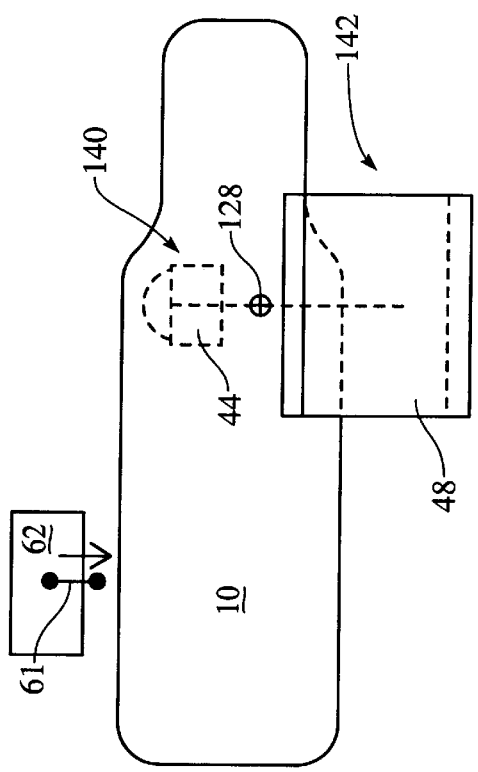
Figure 5B:
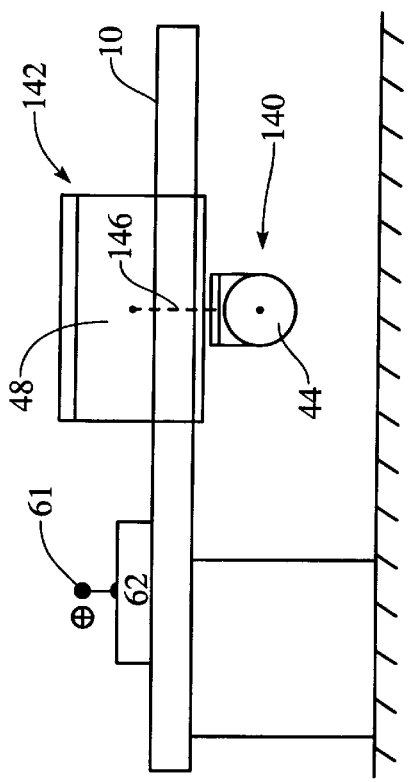

Turning now to FIGS. 5a–c, the x-ray source and detector pair are shown in a second set of first and second positions 140, 142, respectively. As shown best in FIG. 5a, the first joystick 61 is deflected toward the left side of the patient couch 10. Movement of the joystick in that manner generates an x-ray beam angulation signal used by the control unit to urge the first and second positioning systems into motion in a manner to carry the x-ray source to the patient's right side on the table along a first arcuate path 144 while maintaining a constant distance d from the isocenter 128. Similarly, the x-ray detector is moved toward the left of the patient table along a second arcuate path 150 while maintaining a constant distance r from the isocenter 128 and oriented in a manner so that a face of the x-ray detector is perpendicular to the x-ray path 146.

Movement of the first joystick 61 along the direction shown in FIGS. 5a–c enables the x-ray source and detector to be oriented into a plurality of sets of first and second positions relative to the patient couch and examination region to enable a range of left and right anterior oblique radiographic images to be generated.

Turning next to FIGS. 6a–c, the x-ray source and detector pair are shown in a third set of first and second positions 170, 172 relative to the patient support couch and examination region. In those figures, the source and detector pair were moved from the ready position illustrated in FIG. 3 by actuation of the first joystick 61 along the compound direction marked in the figures with an arrow and an arrow tail. More particularly, in order to move the source and detector into the positions illustrated, the first joystick 61 is moved at an angle relative to the head and the right side of the patient support table. This generates a compound angulation of the x-ray path through the examination region.

As the first joystick is moved into the position shown, the x-ray source 44 is moved along an arcuate path 174 toward the left side and foot end of the patient support couch while maintaining the x-ray path 146 centered on the isocenter 128. The arcuate path 174 defines a constant distance d between the x-ray source and the isocenter. As the x-ray source is moved into the position shown, the x-ray detector is simultaneously moved by the second positioning system along a second arcuate path 180 while maintaining a constant distance r from the isocenter 128 and while remaining perpendicular to and centered on the x-ray path 146.

The third set of first and second positions 170, 172 of the x-ray source and detector are useful to generate compound angulation radiographic images of a patient disposed on the patient support couch. The third set of positions enable compound anterior oblique, cranial and caudal radiographic images to be collected.

Figure 7:
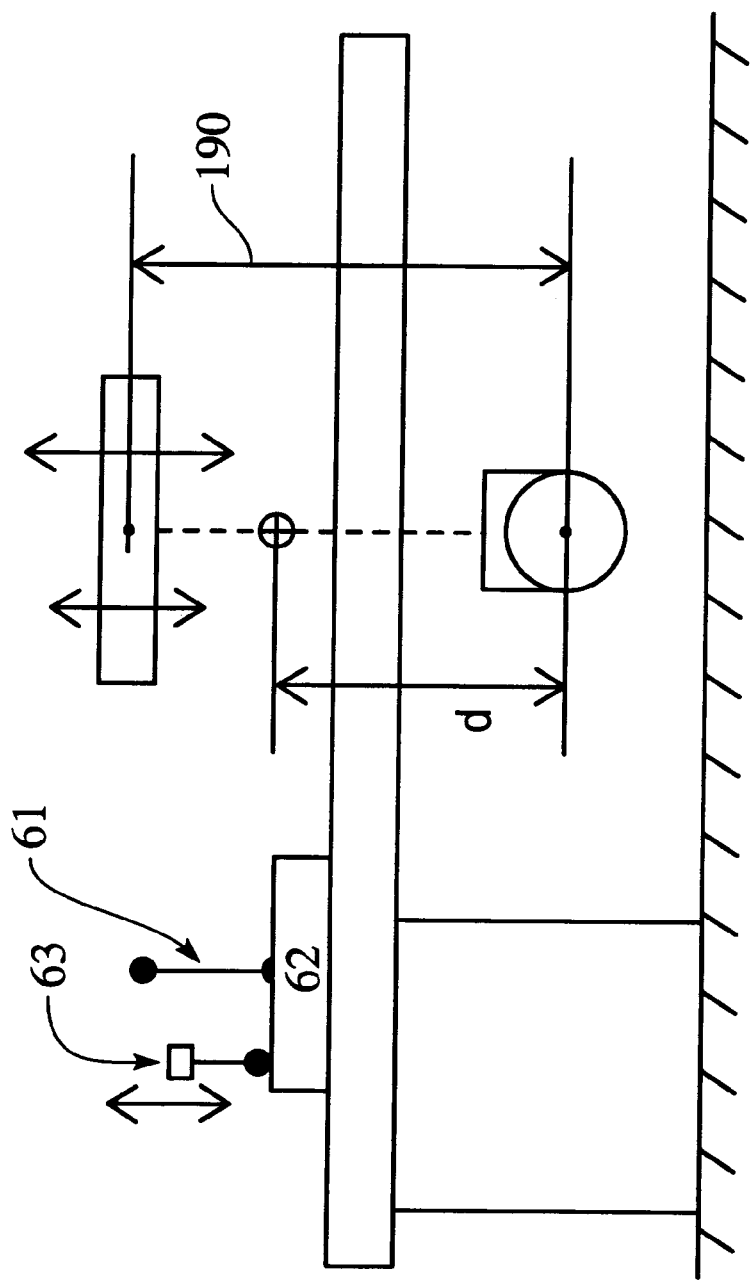
FIG. 7 is a side plan view of the robotic x-ray source and detector positioning system of the present invention oriented in a fourth orientation; and, FIG. 8 is a block diagram of a virtual C-arm robotic positioning system formed in accordance with a second preferred embodiment of the present invention.

Turning next to FIG. 7, the apparatus of the present invention is shown in a mode of operation that enables variation of the source-to-image distance (SID). As shown there, a second joystick 63 is actuated vertically up or down to increase or decrease, respectively, the source-to-image distance. More particularly, when the second joystick 63 is translated vertically downwardly by an operator, the x-ray source and detector are moved relatively closer together to reduce the source-to-image distance 190. Only the x-ray detector is moved toward or away from the x-ray source in order to maintain a constant distance d between the x-ray source and the x-ray beam isocenter 128.

Figure 8:
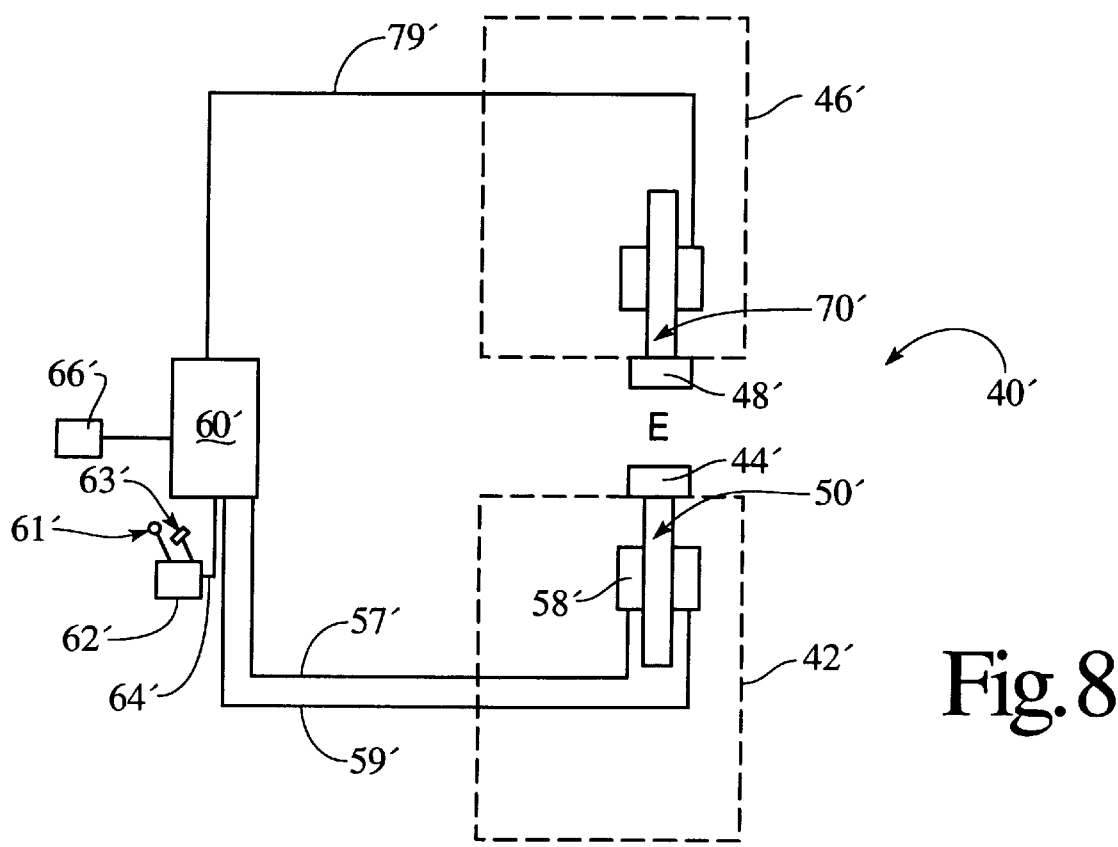

The second preferred embodiment of the invention is shown in FIG. 8 whereat a virtual C-arm support system 40' includes a first positioning system 42' operatively connected to an x-ray source 44' and a second positioning system 46' operatively connected to an x-ray detector 48'. In the second embodiment illustrated, only the first positioning system is adapted to respond to command signals 57' from the control unit 60'. The second positioning system 46' is merely a mechanical support system having multiple movable members that are operatively associated with one or more feedback devices to generate feedback position signals 79' that are used by the control unit to generate the position command signals 67'.

Also in the second preferred embodiment of the invention, the joystick device 62 is not included. Rather, to use the system, an interventionist merely grasps or otherwise manually moves the second positioning system 46' and x-ray detector carried thereon into a desired position relative to the patient or couch. The virtual C-arm support system 40' is operative to generate the necessary command signals 57' to appropriately position and orient the x-ray source 44' relative to the detector in order to generate suitable radiographic images.

The first positioning system 42' includes a first movable arm assembly 50' having a first end held fixed at a first location relative to the examination region. A free end of the first movable arm assembly 50' is adapted for direct mechanical connection to the x-ray source 44'.

The movable arm assembly includes multiple rotatable, extendable, and pivotable arm segments that are preferably substantially formed identically to those described above in connection with the first preferred embodiment. The first movable arm assembly includes a closed loop servo positioning system 58' for controlling the movement and positioning of the movable arm assembly 50' in response to command signals 57' generated by the control unit 60'.

Similarly, in accordance with the second preferred embodiment of the invention, the second positioning system 46' includes a movable arm assembly 70' that is formed substantially identically to the second positioning system described above in connection with the first preferred embodiment. As noted above, however, the second movable arm assembly is merely a feedback-type system and, accordingly, is not responsive to command signals from the control unit. Rather, the second positioning system generates x-ray detector feedback signals 79' for use by the control unit 60' to suitably position the x-ray source relative to the manually positionable x-ray detector and to the examination region.

In accordance with the second preferred embodiment of the invention, only the first positioning system 42' operates under the command of the control unit 60'. The second positioning system 46' is manually movable. The control unit is in operative command of only the first positioning system to maintain a predetermined spatial relationship between the x-ray source and the manually movable detector through a range of positions of those devices relative to the examination region.

Further in accordance with the second preferred embodiment of the invention, each of the sets of first and second positions of the x-ray source and detector pair described above in connection with FIGS. 4–7 are realizable in the second embodiment by simply manually orienting the x-ray detector into the desired position. In the second embodiment, the x-ray source is automatically moved in response to manual arrangement of the x-ray detector.

The invention has been described with reference to the preferred embodiment. Obviously, modifications and alterations will occur to others upon a reading and understanding of this specification. One alternative, for example is to modify the attachment of the fixed end 52, 72 of the arm assembly to include a slidable connection to the floor and ceiling respectively. The connection could be automated or non-powered. That alteration could enable a larger range of robotic arm motion relative to the examination region. The present application is intended to include all such modifications and alterations insofar as they come within the scope of the appended claims or the equivalents thereof.

Having thus described the invention, it is claimed:

1. A virtual C-arm support system for use in a radiographic imaging apparatus of the type including an x-ray source adapted to transmit an x-ray beam along a path through an examination region and an x-ray detector adapted to receive the x-ray beam and generate electric signals indicative of an intensity of the received x-ray beam, the virtual C-arm system comprising:
   a first positioning system connected to the x-ray source for selectively positioning the x-ray source in a range of first orientations relative to the examination region;
   a second positioning system connected to the x-ray detector for selectively positioning the x-ray detector in a range of second orientations relative to the examination region; and,
   a control unit in operative command of at least one of the first and second positioning systems to maintain a predetermined spatial relationship between the x-ray source and the x-ray detector for each of said ranges of first and second orientations relative to the examination region.

2. The virtual C-arm support system according to claim 1 wherein:
   the first positioning system is responsive to a first command signal to move the x-ray source relative to the examination region based on the first command signal;
   the second positioning system is responsive to a second command signal to move the x-ray detector relative to the examination region based on the second command signal; and,
   the control unit is in operative command of both the first positioning system and the second positioning system and is adapted to selectively generate said first and second command signals to respectively position the x-ray source and the x-ray detector at a plurality of sets of first and second positions in relative alignment with each other on opposite sides of the examination region so that at each of said plurality of sets of first and second positions, the x-ray beam transmitted from the x-ray source passes through the examination region and so that at each of said plurality of sets of first and second positions, the x-ray detector is disposed along said path of the x-ray beam to intercept the x-ray beam to generate said electric signals indicative of the intensity of the received x-ray beam.

3. The virtual C-arm support system according to claim 2 wherein:
   the first positioning system is a first movable arm assembly having a first end held fixed at a first location relative to the examination region and a free end adapted for connection to the x-ray source, the first movable arm assembly being responsive to said first command signal from the control unit to selectively orient the x-ray source relative to the examination region; and,
   the second positioning system is a second movable arm assembly having a first end held fixed at a second location relative to the examination region and a free end adapted for connection to the x-ray detector, the second movable arm assembly being responsive to said second command signal from the control unit to selectively orient the x-ray detector relative to the examination region.

4. The virtual C-arm support system according to claim 3 wherein:
   the control unit is adapted to generate first and second position command signals to selectively control said path of the x-ray beam transmitted through the examination region;
   the first movable arm assembly includes a first multi-segmented robotic arm assembly having a closed loop servo positioning system cooperative with the first multi-segmented robot arm to selectively position the x-ray source in said plurality of first orientations relative to the examination region in response to said first position command signal from the control unit; and,
   the second movable arm assembly includes a second multi-segmented robot arm assembly having a closed loop servo positioning system cooperative with the second multi-segmented robotic arm to selectively position the x-ray detector in said plurality of second orientations relative to the examination region in response to said second position command signal from the control unit.

5. The virtual C-arm support system according to claim 4 wherein the control unit:
   is responsive to an x-ray beam angulation signal received from an operatively associated external source to control said path of the x-ray beam by generating said first and second position command signals so that the path of the x-ray beam matches the x-ray beam angulation signal; and,
   is adapted to generate an x-ray beam path indicia signal representative of said path of the x-ray beam through the examination region.

6. The virtual C-arm support system according to claim 5 wherein:
   the control unit is responsive to an x-ray beam angulation signal received from an operatively associated joystick operable by a human operator;
   the first end of the first multi-segmented robotic arm assembly is floor supported and is held fixed relative to a patient table adjacent the examination region; and,
   the first end of the second multi-segmented robotic arm assembly is ceiling supported and is held fixed relative to the patient table adjacent the examination region.

7. A virtual C-arm support system for use in a radiographic imaging apparatus of the type including an x-ray source adapted to transmit an x-ray beam along a path through an examination region and an x-ray detector adapted to receive the x-ray beam and generate electric signals indicative of an intensity of the received x-ray beam, the virtual C-arm system comprising:
   a first positioning system connected to the x-ray source for selectively positioning the x-ray source in a range of first orientations relative to the examination region, the first positioning system being responsive to a first command signal to move the x-ray source relative to the examination region based on the first command signal;
   a second positioning system connected to the x-ray detector for selectively positioning the x-ray detector in a range of second orientations relative to the examination region, the second positioning system being adapted to generate an x-ray detector orientation feedback signal representative of the relative orientation between the x-ray detector carried on the second positioning system and said examination region; and, a control unit in operative command of at least one of the first and second positioning systems to maintain a predetermined spatial relationship between the x-ray source and the x-ray detector for each of said ranges of first and second orientations relative to the examination region, the control unit being in operative control of the first positioning system and adapted to selectively generate said first command signal used by the first positioning system to control the path of the x-ray beam transmitted through the examination region based on said x-ray detector feedback orientation signal to maintain said predetermined spatial relationship between the x-ray emitter and the x-ray detector.

8. The virtual C-arm support system according to claim 7 wherein:

the first positioning system is a first movable arm assembly having a first end held fixed at a first location relative to the examination region and a free end adapted for connection to the x-ray source, the first movable arm assembly being responsive to said first command signal from the control unit to selectively orient the x-ray source relative to the examination region; and, the second positioning system is a second movable arm assembly having a first end held fixed at a second location relative to the examination region and a free end adapted for connection to the x-ray detector, the second movable arm assembly being manually movable by a human operator to selectively orient the x-ray detector relative to the examination region.

9. A positioning system for an x-ray source and an x-ray detector in a radiographic imaging apparatus, the positioning apparatus comprising:

a first robotic support member having a first fixed end and a free end, the first robotic support member being responsive to a first position command signal to move the free end relative to the fixed end;

a second robotic support member having a fixed end and a free end, the second robotic support member being responsive to a second position command signal to move the free end relative to the fixed end;

an x-ray source carried on the first support member and adapted to transmit an x-ray beam along a path through an examination region;

an x-ray receptor carried on the second support member and adapted to receive the x-ray beam and generate electric signals indicative of an intensity of the received x-ray beam; and, a control unit operatively connected to the first robotic support member and the second robotic support member, the control unit being adapted to generate said first and second position command signals to move the first support member and the second support member into first and second positions, respectively, relative to the examination region, with a predetermined spatial relationship between the x-ray source and the x-ray detector, to enable the radiographic imaging apparatus to produce a radiographic image.

10. The positioning system according to claim 9 wherein the first and second robotic support members are adapted to move the x-ray source and the x-ray receptor through respective first and second arcuate paths to respective first and second positions relative to the examination region to enable the radiographic imaging apparatus to produce said radiographic image.

11. The positioning system according to claim 10 wherein the control unit is adapted to generate said first and second command signals to maintain a predetermined relative distance between the x-ray source and the x-ray receptor.

12. The positioning system according to claim 11 wherein the control unit is adapted to generate said first and second command signals in response to an x-ray beam angulation signal generated from an operatively associated external manual joystick device.

13. The positioning system according to claim 12 wherein the control unit is adapted to move the x-ray source and the x-ray receptor through said respective first and second arcuate paths to respective first and second positions to enable the radiographic imaging apparatus to produce a one of a left and right anterior oblique view of a human body disposed in said examination region.

14. The positioning system according to claim 12 wherein the control unit is adapted to move the x-ray source and the x-ray receptor through said respective first and second arcuate paths to respective first and second positions to enable the radiographic imaging apparatus to produce a one of a caudal and cranial view of a human body disposed in said examination region.

15. The positioning system according to claim 12 wherein the fixed end of the first robotic support member is carried on a support adapted to enable linear motion of the first robotic support member.

16. A diagnostic imaging apparatus comprising:

an x-ray source adapted to transmit an x-ray beam through an examination region;

an x-ray detector adapted to receive the x-ray beam and generate electric signals indicative of an intensity of the received x-ray beam;

a first mechanical arm assembly adapted to carry the x-ray detector, the first mechanical arm assembly being manually movable to hold the x-ray detector in a plurality of first positions relative to the examination region;

a second mechanical arm assembly adapted to carry the x-ray source, the second mechanical arm assembly being responsive to a motion command signal to selectively position the x-ray source at a plurality of second locations relative to the examination region; and, a control unit operatively associated with the first and second mechanical arm assemblies and adapted to generate said motion command signal based on a location of said x-ray detector in said plurality of first positions to maintain a predetermined spatial relationship between the x-ray source and the x-ray detector.

17. A diagnostic imaging apparatus comprising:

an x-ray source adapted to transmit an x-ray beam through an examination region;

an x-ray detector adapted to receive the x-ray beam and generate electric signals indicative of an intensity of the received x-ray beam;

a first mechanical arm assembly adapted to carry the x-ray detector, the first mechanical arm assembly being manually movable to hold the x-ray detector in a plurality of first positions relative to the examination region, the first mechanical arm assembly being adapted to generate a position feedback signal indicative of a first position of the x-ray detector relative to the examination region;

a second mechanical arm assembly adapted to carry the x-ray source, the second mechanical arm assembly being responsive to a motion command signal to selectively position the x-ray source at a plurality of second locations relative to the examination region; and, a control unit operatively associated with the first and second mechanical arm assembly and adapted to generate said motion command signal based on a location of said x-ray detector in said plurality of first positions, the control unit being adapted to receive said position feedback signal and generate said motion command signal to move the x-ray source to a second position relative to a position of the x-ray detector.

18. The diagnostic imaging apparatus according to claim 17 wherein the control unit is adapted to generate said motion command signal to maintain a predetermined spacial relationship between the x-ray source and the x-ray detector.

19. The diagnostic imaging apparatus according to claim 18 wherein the second mechanical arm assembly is adapted to carry the x-ray source on a first end and includes a second end carried on a support adapted to enable linear motion of the second mechanical arm assembly relative to the examination region.

20. In a radiographic imaging apparatus of the type including an x-ray source transmitting an x-ray beam along a path through an examination region and an x-ray detector receiving the x-ray beam and generating electric signals indicative of an intensity of the received x-ray beam, a method of positioning the x-ray source and the x-ray detector relative to the examination region comprising the steps of:

using a first positioning system operatively associated with the x-ray source, positioning the x-ray source in a range of first orientations relative to the examination region in response to a first command signal;

using a second positioning system operatively associated with the x-ray detector, positioning the x-ray detector in a range of second orientations relative to the examination region and generating an x-ray detector orientation feedback signal representative of the relative orientation between the x-ray detector and said examination region; and, using a control unit, generating said first command signal used by the first positioning system to control the path of the x-ray beam transmitted through the examination region based on said x-ray detector feedback orientation signal to maintain a predetermined spatial relationship between the x-ray emitter and the x-ray detector for each of said ranges of first and second orientations relative to the examination region.

21. The method according to claim 20 further comprising the steps of:

manually moving the second positioning system by a human operator to selectively position the x-ray detector in a range of third orientations relative to the examination region; and, using said control unit, generating said first command signal used by the first positioning system to control the path of the x-ray beam transmitted through the examination region based on said x-ray detector feedback orientation signal to maintain said predetermined spatial relationship between the x-ray emitter and the x-ray detector for said range of third orientations of the x-ray detector relative to the examination region.

22. A diagnostic imaging method comprising:

transmitting an x-ray beam generated by an x-ray source through an examination region;

receiving the x-ray beam at an x-ray detector and generating electric signals indicative of an intensity of the received x-ray beam;

manually moving a first mechanical arm assembly carrying the x-ray detector to hold the x-ray detector in a first position relative to the examination region;

generating a position feedback signal indicative of said first position of the x-ray detector relative to the examination region;

using a second mechanical arm assembly carrying the x-ray source, selectively positioning the x-ray source at locations relative to the examination region in response to a motion command signal; and, in a control unit operatively associated with the first and second mechanical arm assemblies, receiving said position feedback signal indicative of said x-ray detector in said first position and generating said motion command signal to move the x-ray source to a second position relative to a position of the x-ray detector.

23. The method according to claim 22 wherein the step of generating said motion command signal includes generating said motion command signal to maintain a predetermined spacial relationship between the x-ray source and the x-ray detector.

24. The according to claim 23 wherein the step of selectively positioning the x-ray source at locations relative to the examination region in response to said motion command signal includes moving the second mechanical arm assembly along a linear path relative to the examination region.

* * * * *